United States Patent [19]

Boaz

[11] Patent Number: 5,250,743
[45] Date of Patent: Oct. 5, 1993

[54] METHOD OF INTERCOVERSION OF ENANTIOMERS OF ACYCLIC 1,2-DIHYDROXY-3-ALKENES

[75] Inventor: Neil W. Boaz, Waterloo, N.Y.

[73] Assignee: Eastman Kodak Company, Rochester, N.Y.

[21] Appl. No.: 999,240

[22] Filed: Dec. 31, 1992

[51] Int. Cl.$^5$ .................. C07C 41/03; C07C 27/00
[52] U.S. Cl. .................. 568/678; 568/618; 568/833; 568/867
[58] Field of Search ............... 568/622, 867, 618, 833, 568/678

[56] References Cited

U.S. PATENT DOCUMENTS

| | | | |
|---|---|---|---|
| 1,641,710 | 9/1927 | Untiedt | 568/867 |
| 1,875,312 | 8/1932 | Youtz | 568/867 |
| 3,932,531 | 1/1976 | Kurata et al. | 568/816 |
| 3,959,389 | 5/1976 | Kurata et al. | 568/867 |
| 4,277,632 | 7/1981 | Kumazawa et al. | 568/867 |
| 4,504,685 | 3/1985 | Vaughan | 568/678 |
| 4,543,430 | 9/1985 | Falgoux et al. | 568/678 |
| 4,551,566 | 11/1985 | Robson et al. | 568/867 |
| 4,560,813 | 12/1985 | Collier | 568/872 |
| 4,593,142 | 6/1986 | Yang | 568/618 |
| 4,626,603 | 12/1986 | Siegmeier et al. | 568/833 |
| 4,801,759 | 1/1989 | Siegmeier | 568/833 |
| 4,933,502 | 6/1990 | Edwards | 568/618 |
| 4,960,952 | 10/1990 | Kemp | 568/618 |

FOREIGN PATENT DOCUMENTS 226799 11/1985 European Pat. Off. .
257243 8/1986 European Pat. Off. .
61-271229 5/1985 Japan .

OTHER PUBLICATIONS

Marshall, J. A. et al., "Highly Antiselective S$_N$2' Additions of LiMe$_2$Cu to Chiral Acyclic Vinyloxiranes", Tetrahedron Lett., 1988, 29, 913.
A. M. Ross et al., "Vinyl Epoxide Hydrolysis Reactions", J. Am. Chem. Soc. 1982, 104, pp. 1658–1665.
T. H. Lowry et al., Mechanism and Theory in Organic Chemistry, pp. 315–320 2nd edition 1981.

Primary Examiner—Werren B. Lone
Attorney, Agent, or Firm—Judith A. Roesler

[57] ABSTRACT

In accordance with the present invention, a method for the interconvertion of the enantiomers of acyclic 1,2-dihydroxy-3-alkenes or for converting either enantiomer of acylic 1,2-dihydroxy-3-alkenes to the corresponding antipodal 1-hydroxy-2-alkoxy-3-alkene compounds has been discovered, comprising reacting in an acidic reaction media either enantiomer of an acylic vinyl epoxide (which can be derived from the corresponding acyclic 1,2-dihydroxy-3-alkene) with water, alcohol, or a mixture thereof. When substantially optically pure acyclic vinyl epoxide compounds are employed in the inventive method, the interconverted acyclic 1,2-dihydroxy-3-alkene or 1-hydroxy-2-alkoxy-3-alkene compound products are also substantially optically pure.

20 Claims, No Drawings

METHOD OF INTERCOVERSION OF ENANTIOMERS OF ACYCLIC 1,2-DIHYDROXY-3-ALKENES

FIELD OF THE INVENTION

The present invention relates to a method for the interconversion of enantiomers of acyclic 1,2-dihydroxy-3-alkenes. In addition, this methodology can convert acyclic 1,2-di-hydroxy-3-alkenes to the antipodal 1-hydroxy-2-alkoxy-3-alkenes. The resulting products are useful chemical intermediates that may be employed in the synthesis of many enantiomerically enriched compounds including pharmaceuticals and agricultural chemicals.

BACKGROUND OF THE INVENTION

There are many different methods that may be used to resolve racemic compounds. The use of enzymes derived from biological systems (for example, from a microorganism or an animal organ) have been particularly useful in the resolution of racemic compounds to form substantially optically pure (enantiomerically enriched) compounds.

In biocatalytic resolution systems, a chiral compound composed of two enantiomers is used as the substrate for the enzyme. The enzyme recognizes and favors only one of the enantiomers as the substrate for the enzymatic reaction. The stereoselectivity of the enzyme optimally affords a product mixture having 50% conversion to a single enantiomer product and 50% recovered substrate of opposite configuration (commonly referred to as an "antipode"). The success of a resolution procedure is determined by the optical purities obtained.

For an enzymatic kinetic resolution, the optical purities of the product and recovered substrate define the degree of enantioselectivity of the reaction and can be expressed as the "E" value. The "E" value is a directly proportional measurement of the R to S reactivity rate ratio, with higher optical purities for product and recovered substrate affording higher "E" values. Because the "E" value is independent of conversion, it is particularly useful in evaluating kinetic resolutions where optical purities can change depending on the extent of reaction. (Chen, C. S., et al., *J. Am. Chem. Soc.*, 1982, 104, p. 7249.)

For present purposes, "substantially optically pure compounds" are enantiomerically enriched compounds defined as having an enantiomeric excess ("ee") value of greater than about 80%±2%. Enantiomeric excess ("ee") is the absolute value of % R minus % S and is used interchangeably with optical purity.

One typical consequence of a biocatalytic resolution process is the 50% maximum yield of each enantiomer. This limitation is particularly problematic if one enantiomer is more useful than its antipode. Frequently, an unwanted antipode is considered a "waste" material.

As with any product mixture resulting from a biocatalytic resolution system, interconversion of the unwanted enantiomer from the product mixture to the desired enantiomer (or at the very least racemization for recycling purposes) would be highly desirable to maximize yield and minimize cost of a useful product. It would be especially useful to develop a method of interconversion having high stereoselectivity to convert one enantiomer to the substantially optically pure antipodal product.

An example of a biocatalytic resolution process in which the interconversion process would be useful, for example, is with preparations involving 3-butene-1,2-diol (shown as structures 1 and 2 below, hereinafter referred to as "BDO").

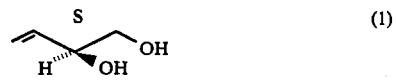

S-BDO

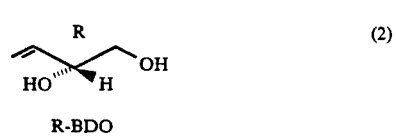

R-BDO

As BDO is an especially useful chiral synthon, interconversion of the R- and S- BDO enantiomers, shown above as structures 1 and 2, would greatly enhance the versatility and utility of the biocatalytic preparation. The interconversion of BDO must rely in some manner on an inversion of configuration at the allylic carbon of a BDO derivative, most efficiently the corresponding epoxide, epoxybutadiene ("EpB" which may be readily prepared from BDO, or various derivatives, without loss of optical purity). Typically, inversion of configuration is approached using a concerted $S_N2$ (nucleophilic) process rather than an $S_N1$ process since $S_N1$ (ionizing) conditions normally lead to racemization, especially with allylic electrophiles (such as EpB) which afford stabilized carbocations. The allylic nature of EpB, however, presents complications for the inversion processes because three of the four carbons of EpB have significant electrophilic reactivity. Thus, a useful $S_N2$ interconversion process for EpB must be both highly stereoselective for inversion and yet regioselective for the chiral (allylic) center.

It is well known that more basic reaction conditions favor $S_N2$ processes while $S_N1$ reactions are favored at lower pH. (Lowry, T. H. and Richardson, K. S., "Mechanism and Theory in Organic Chemistry," Harper and Row Publishers, New York; 1981, pp.323-330.) The simplest $S_N2$ method with a potential for stereoselective inversion of EpB to form BDO is reacting the epoxide with hydroxide ion. However, it has been found that a similar nucleophilic opening of the epoxide of EpB with methoxide under basic conditions proceeds with high regioselectivity for the undesired primary epoxide terminus, thus encouraging retention of configuration. (Parker, R. E.; Isaacs, N. S., *Chem. Rev.* 1975, p. 737 and Smith, J. G., *Synthesis*, 1984, p. 629.) Indeed, reaction of S-EpB with sodium hydroxide affords BDO of only 30% ee, indicating significant reactivity at both epoxide carbons.

Although EpB can be opened under neutral or acidic conditions, it is known that as the reaction media becomes more acidic and ionizing, $S_N1$ processes (initial ionization) are favored. An $S_N1$ reaction would be expected to result in poor stereoselectivity, because once the epoxide opens to the corresponding stabilized allylic carbocation, the epoxide would be expected to rapidly and largely racemize. (Lowry, T. H. and Richardson, K. S. "Mechanism and Theory in Organic Chemistry", Harper and Row Publishers, New York; 1981, pp. 315-320; and Ross, A. M.; Pohl, T. M.; Piazza, K.;

Thomas, M.; Fox, B.; Whalen, D. L., *J. Am. Chem. Soc.*, 1982, 104, p. 1658.) Stereochemical scrambling due to the intermediacy of the allylic carbocation in systems closely related to EpB [such as cyclopentadiene monoepoxide (3)] has been observed. As shown below, hydrolysis of cyclopentadiene monoepoxide (3) under acidic conditions affords all four possible products, cis-4, trans-4, cis-5, trans-5 in a ratio of 25:16:16:43, respectively. (Ross, A. M.; Pohl, T. M.1 Piazza, K.; Thomas, M.; Fox, B.; Whalen, D. L. *J. Am. Chem. Soc.* 1982, 104, p. 1658.) Thus, literature precedent indicates that the hydrolytic opening of vinyl epoxides under $S_N1$ conditions is largely stereorandom.

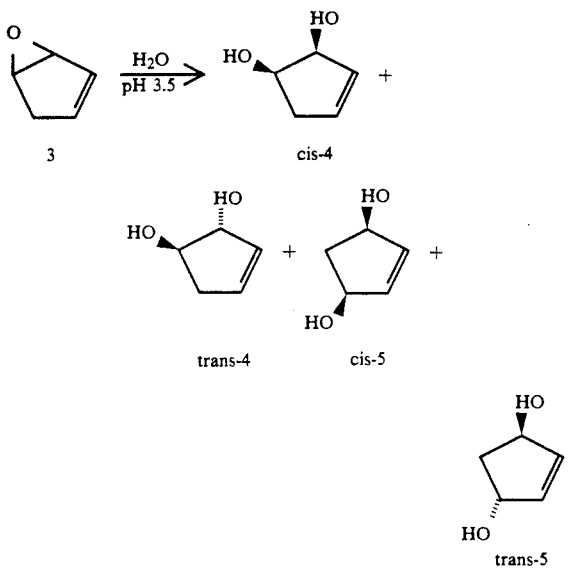

It has also been reported that the product distribution for the opening of EpB under neutral or acidic conditions differs from the product distribution under basic conditions. Acidic conditions result in high regioselectivity for the secondary allylic position, with a small amount of primary allylic product (2-butene-1,4-diol) (Petrov, V. A., et al., *Zh. Organ. Khim.*, 1984, 20, 993.) The presence of only minor amounts of primary allylic products has been suggested as indicative of an A-2-like (bimolecular) transition state. (Ross et al., *J. Am. Chem Soc.*, 1982, 104, 1658.) This, however, may just reflect the relative thermodynamic stabilities of the secondary versus the primary positions and therefore the amount of cationic character at each position. Notwithstanding, the presence of the two allylic products indicates that the transition state involves allylic C-O bond cleavage with a significant amount of carbocation character. Accordingly, an even more thoroughly racemized product than that obtained using basic conditions would be expected when opening acyclic vinyl epoxides using acidic conditions.

Discovering a method for the interconversion of these enantiomeric species while substantially maintaining the optical integrity of the products is needed.

SUMMARY OF THE INVENTION

In accordance with the present invention, a method for the interconversion of enantiomers of an acyclic 1,2-dihydroxy-3-alkene or converting either enantiomer of an acylic 1,2-dihydroxy-3-alkene to a corresponding antipodal 1-hydroxy-2-alkoxy-3-alkene compound has been discovered comprising reacting in an acidic reaction media either enantiomer of an acylic vinyl epoxide (which can be derived from the corresponding acyclic 1,2-dihydroxy-3-alkene) with water, an alcohol, or a mixture thereof to form a product comprising an inverted acyclic 1,2-dihydroxy-3-alkene or an inverted 1-hydroxy-2-alkoxy-3-alkene compound.

In the first embodiment of this invention, the discovered method for the interconversion of enantiomers of an acyclic 1,2-dihydroxy-3-alkene compound comprises reacting in an acidic reaction media either enantiomer of an acylic vinyl epoxide with water to form a product comprising an inverted 1,2-dihydroxy-3-alkene compound.

In the second embodiment of this invention, a method for converting an enantiomer of an acylic 1,2-dihydroxy-3-alkenes to corresponding antipodal 1-hydroxy-2-alkoxy-3-alkene compounds has been discovered, the method comprising reacting in an acidic reaction media either enantiomer of an acylic vinyl epoxide with an alcohol to form an inverted acyclic 1-hydroxy-2-alkoxy-3-alkene compound.

When substantially optically pure acyclic vinyl epoxide compounds are employed in the inventive method, the interconverted acyclic 1,2-dihydroxy-3-alkene or 1-hydroxy-2-alkoxy-3-alkene compound products are also substantially optically pure.

Unexpectedly, a method for the inversion of configuration of enantiomers of acyclic vinyl epoxides has been discovered. At contrast with results at high pH, at low pH (where a thoroughly racemized product was expected) rapid formation of a product displaying highly selective inversion of configuration at the allylic carbon has been discovered. Indeed, the stereoselectivity was higher at low pH than at neutral pH. Thus, this method results in a high yield of substantially optically pure product (when a substantially optically pure acylic vinyl epoxide is employed), with an acceptable reaction rate.

DETAILED DESCRIPTION OF THE INVENTION

The optical purity of the interconverted product produced by this invention is dependent upon the optical purity of the acyclic vinyl epoxide enantiomer reacted with the water or alcohol (or mixture thereof) and to a lesser extent on the alcohol or water selected as a reactant. Preferably, to form a substantially optically pure inverted product, substantially optically pure acyclic vinyl epoxide enantiomers are used.

Acyclic vinyl epoxides that may be interconverted using this method include either enantiomer of the acyclic vinyl epoxides of the following Formula I:

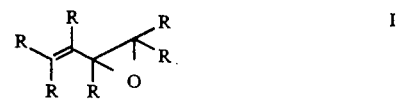

wherein R independently represents a straight or branched, substituted or unsubstituted, $C_1$-$C_{20}$ alkyl, $C_2$-$C_{20}$ alkenyl, or a $C_2$-$C_{20}$ alkynyl group, or a substituted or unsubstituted $C_4$-$C_{10}$ aromatic or heteroaromatic group (with the hetero atom selected from nitrogen, sulfur, or oxygen), with said substituents designated above selected from one or more of the following: halogen, a cyano, a $C_1$-$C_5$ alkoxy, a $C_1$-$C_5$ alkylthio, a $C_1$–$C_5$ ether group, a $C_1$–$C_5$ ester group, a nitro group, a $C_1$–$C_5$ ketone group, or a $C_1$–$C_5$ thioether group.

More preferably, the epoxide is substantially pure and represented by either enantiomer of Formula II as follows:

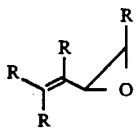

wherein R is as defined previously.

Most preferably, the epoxide is substantially optically pure and represented by either enantiomer of Formula III below:

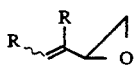

wherein R is as defined previously.

Substantially optically pure acyclic vinyl epoxides or other precursors may be prepared by various known methods, including, for example, chemoenzymatic preparation (as described, for example, in U.S. Ser. No. 854,944, filed Mar. 20, 1992, by N. Boaz); classical chemical resolution; and (as described in Marshall, J. A. et al., Tetrahedron Lett., 1988, 29, 913) Sharpless asymmetric epoxidation of an allylic alcohol, followed by the oxidation of the alcohol to an aldehyde and olefination (simplified for purposes of illustration by Reaction Scheme 1, as follows).

Reaction Scheme 1

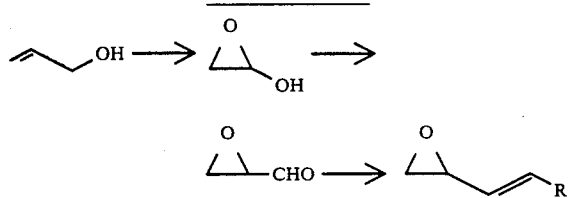

Although the method of preparation of the epoxide is largely immaterial to the present invention, the invention is particularly useful in a biocatalytic resolution process, involving for example, BDO, as depicted by Reaction Schemes 2 and 3 below.

Reaction Scheme 2 shows the process by which a substantially optically pure hydroxy-tosylate (6) may be prepared from BDO.

Reaction Scheme 2

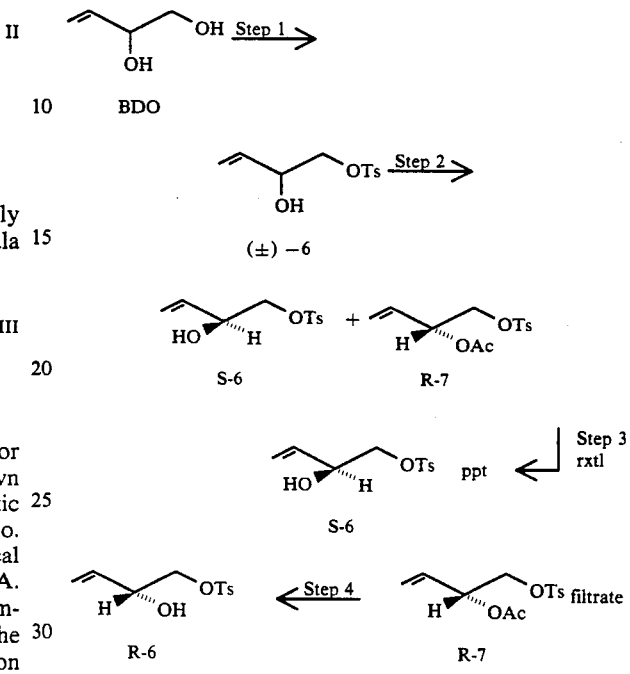

As shown above, in step 1 of Reaction Scheme 2, BDO is converted to (±)-hydroxy-tosylate [(±)-6] using with methods well-known to those skilled in the art. In step 2, (±)-6 is then enzymatically resolved to S-hydroxy-tosylate (S-6) and R-acetoxy-tosylate (R-7) by any number of methods, such as that described in pending U.S. application Ser. No. 854,944. In Step 3, S-6 is separated from R-7 by the recrystallization of the mixture twice to afford substantially optically pure (S)-hydroxy-tosylate S-6 (ppt) and the impure enantiomerically enriched (R)-acetoxy-tosylate R-7(filtrate). In step 4, the substantially optically pure (R)-hydroxy-tosylate R-6 may be obtained from the (R)-acetoxy-tosylate R-7 by chemical removal of contaminants, acid hydrolysis of the acetate, and recrystallization as described, for example, in U.S. Pat. No. 5,126,268.

Reaction Scheme 3 illustrates how hydroxytosylate 6 (either enantiomer) may be further converted to BDO.

Reaction Scheme 3

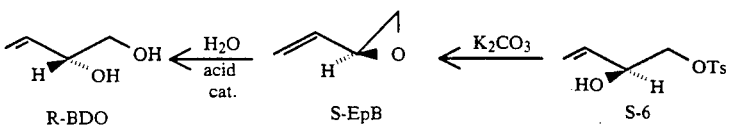

-continued
Reaction Scheme 3

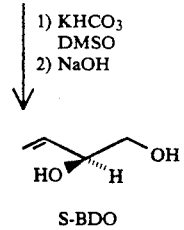

S-BDO

As shown, Reaction Scheme 3 describes how hydroxytosylate 6 (either enantiomer) may be converted to BDO (same configuration) by a two step sequence: (1) KHCO₃, DMSO, 60° C.; and (2) aq. NaOH. Also shown by Reaction Scheme 3, the substantially optically pure hydroxy-tosylate 6 may be converted to the antipodal BDO by conversion to epoxide (K₂CO₃) followed by acid-catalyzed water addition (inversion of configuration) according to this invention.

An illustration of the usefulness of the invention is shown by Reaction Scheme 4, immediately hereafter. This reaction scheme is just one of many that may employ the present invention. The inventive step is shown as Steps 2 and 5. As used in the diagram: R-6 represents R-1-tosyloxy-2-hydroxy-3-butene; R-BDO and S-BDO represent the R and S entantiomers of 3-butene-1,2-diol; R-EpB and S-EpB represent the R and S entantiomers of epoxybutene; S-6 represents S-1-tosyloxy-2-hydroxy-3-butene; TsCl represents toluenesulfonyl chloride; and rxtl indicates a recrystallization occurred.

Reaction Scheme 4

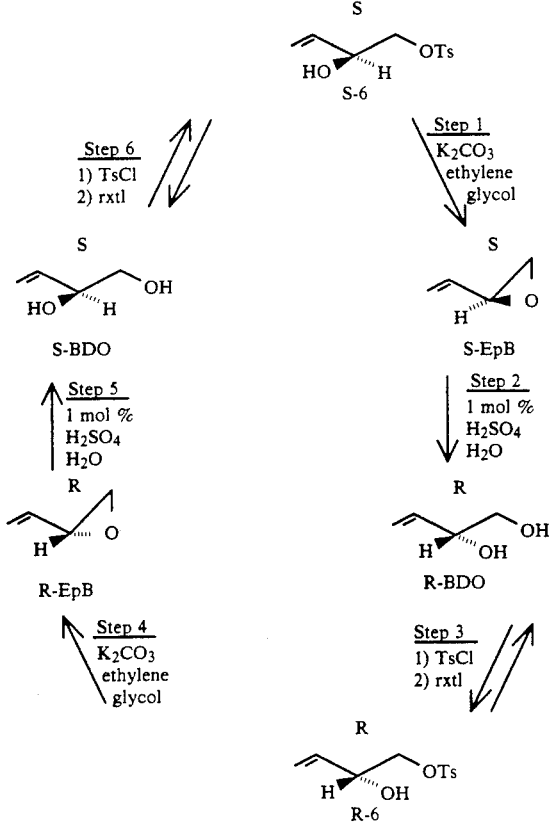

As shown in Reaction Scheme 4, steps 4, 5, and 6 are the same as steps 3, 2, and 1, respectively. The scheme demonstrates how any one of the six compounds can be converted into any of the others. Steps 1 and 4 show the formation of an epoxide. Steps 2 and 5 show an embodiment of the invention, where an inversion of configuration occurs during hydrolysis. In the forward direction of steps 3 and 6, the preparation of a tosylate is shown. In the reverse direction of step 3 and 6 conversion of tosylate to diol is shown.

According to the invention, the reaction media is acidic. Preferably, the reaction media is prepared to have a pH level within the range of $-5$ to 7, more preferably within the range of 0 to 7, and most preferably from 0 to 3. Any Bronsted acid or Lewis acid and mixtures thereof (also referred to herein as "acid catalyst") may be used to make the reaction media acidic. More preferably used as an acid catalyst are mineral acids, sulfuric acid, nitric acid, organic sulfonic acids, sulfonic acid resins, carboxylic acids (such as trifluoroacetic acid, trichloroacetic acid, benzoic acid, and so on), and mixtures thereof. Most preferably, the acid is selected from sulfuric acid, organic sulfonic acids, sulfonic acid resins, and strong carboxylic acids with a pKa of $<3$. Although not essential, preferably the reaction media is made acidic prior to the contacting of the acyclic vinyl epoxide.

As previously defined, the acyclic vinyl epoxide is reacted with water, an alcohol, or a mixture of both. Preferably the alcohol is defined by the formula R'OH wherein R' represents an unsubstituted or substituted, straight or branched $C_1-C_{20}$ alkyl, $C_2-C_{20}$ alkenyl, or $C_2-C_{20}$ alkynyl group or an unsubstituted or substituted $C_4-C_{20}$ aromatic group (with said substituents designated above selected from one or more of the following: a halogen, a cyano, a $C_1-C_5$ alkoxy, a $C_1-C_5$ alkylthio, a $C_1-C_5$ ether group, a $C_1-C_5$ ester group, a nitro group, a $C_1-C_5$ ketone group, or a $C_1-C_5$ thioether group. More preferably reacted with the epoxide is either water or an alcohol wherein R' represents a $C_1-C_6$ straight or branched alcohols (such as methanol, ethanol, n-propanol, i-propanol, n-butanol, s-butanol, i-butanol). A mixture of of water and alcohols may be used in the reaction media, however a mixture of products may result.

The ratio of the alcohol, water, or mixture thereof to acyclic vinyl epoxide substrate effective in this invention is highly variable. Preferably, the amount of water and/or alcohol is from 1 equivalent to a large excess. Preferably, the epoxide and water and/or alcohol are reacted in an appropriate solvent, as known to those skilled in the art. The water and/or alcohol component selected as a reactant may also be used as a solvent.

Preferably, the reaction media is maintained at a low temperature. This low temperature facilitates the selectivity of the inversion reaction. Preferably the reaction media is at a temperature as low as possible while maintaining the reaction media as a liquid and affording an acceptable reaction rate. As used herein an acceptable reaction rate is defined as a reaction having at least 80% (more preferably 90% and most preferably 95%) of the acyclic vinyl epoxide substrate consumed within about 48 hours (more preferably 24 hours and most preferably 12 hours), as detectable by methods known to those skilled in the art including for example vpc (vapor phase chromatography), tlc (thin layer chromatography), $^1$H nmr (nuclear magnetic resonance), and so on. The reaction media temperature preferably ranges from about $-100°$ C. to about $+100°$ C. More preferably, the temperature falls within the range from about $-20°$ C. to about $50°$ C. Most preferably, the temperature of the reaction media is maintained within a range of about $0°$ C. to about $25°$ C.

Although not essential, preferably the reaction media is neutralized prior to the recovery of the inverted product. Neutralization may be accomplished, if desired, by any known technique, such as, for example, the addition of aqueous or solid sodium bicarbonate (preferably to a pH of 7 to 9 for soluble acid catalysts). When employed, sulfonic acid resins may be removed by filtration.

The recovery of the inverted product of this invention may be accomplished by any appropriate method known to those skilled in the art. Preferably, the solvent is removed at reduced pressure. The residue may then be dissolved in a suitable organic solvent (such as, for example, dichloromethane, ethyl acetate, or an ether); dried; and concentrated to afford crude product. The crude product may be purified, if desired, by appropriate methods (such as, for example, distillation, crystallization, chromatography, and so on).

The inverted product of this invention may be represented by either enantiomer of Formula IV or Formula V, as shown below.

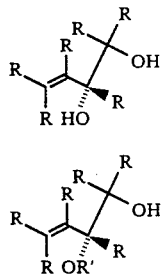

Formula IV results when water is reacted with the epoxide. Formula V results when an alcohol is reacted with the epoxide. As represented in both Formula IV and Formula V, the designations R and R' have the latitude previously defined.

The product produced by this invention may be recovered and used as a commodity chemical as an intermediate for various pharmaceutical or agricultural chemicals. The product may also be manipulated in various chemical reactions for purposes of preparing desired $C_4$ synthons. This invention is particularly useful when a substantially optically pure acyclic vinyl epoxide is the substrate since the optical integrity of the product is maintained during the interconversion process.

The present invention is now further illustrated by, but is by no means limited to, the following examples.

EXAMPLES

Preparation of S-EpB from S-Hydroxy-tosylate S-6

Ethylene glycol (35 mL) was placed in vacuo for 30 minutes to remove any residual water. S-Hydroxy-tosylate S-6 (99% ee; 8.88 g; 36.7 mmol) was added, and the mixture was stirred and sonicated until most had dissolved. Potassium carbonate (6.58 g; 47.6 mmol; 1.3 equiv) was added, and the reaction mixture was stirred for 1 h at room temperature to afford a homogeneous solution with no residual S-6 as determined by tlc (thin layer chromatography) analysis. The product S-EpB was distilled directly from the reaction flask (over 1 h) at ca. 5 mm Hg and collected in a flask cooled to $-78°$ C. The codistilled water was physically removed to afford 2.1423 g (78%) of S-EpB as a clear, colorless liquid. Properties of the EpB are as follows: EpB:

$^1$H nmr (300 MHz, CDCl$_3$): 5.522 (2H, m); 5.298 (2H, m); 3.345 (1H, quintet, J=3.15 Hz); 2.967 (1H, t, J=4.43 Hz); 2.657 (1H, dd, J=2.31, 5.17 Hz).

$[\alpha]D^{20}+20.2°$ (c. 0.872, pentane).

Determination of Optical Purity of BDO

In the examples where BDO was the product (water addition), the optical purity was determined by conversion to 1-tosyloxy-2-hydroxy-3-butene (6), followed by derivatization of the secondary alcohol as its S-$\alpha$-methoxy-$\alpha$-trifluoromethylphenylacetate and $^1$H nmr analysis, as described below. Optically active R-BDO (40 mg; 0.45 mmol) was dissolved in pyridine (1 mL) and cooled to $0°$. p-Toluenesulfonyl chloride (p-TsCl; 82 mg; 0.43 mmol; 0.95 equiv) was added, and the reaction mixture was thoroughly stirred. The reaction was placed at $4°$ C. overnight and then diluted with ether (25 mL), washed with H$_2$O (10 mL), 3 N HCl (3×10 mL), and NaHCO$_3$ (10 mL). The ethereal solution was dried (with MgSO$_4$) and concentrated to afford 50 mg (46%) of R-hydroxy-tosylate R-6. A portion of R-hydroxytosylate R-6 (16 mg; 0.066 mmol) was dissolved in methylene chloride (1 mL). 4-Dimethylaminopyridine (DMAP; 24 mg; 0.20 mmol; 3 equiv) was added, followed by S-MTPA-Cl (S-$\alpha$-methoxy-$\alpha$-trifluoromethylphenylacetyl chloride)(24 μL; 0.13 mmol; 2 equiv). The reaction mixture was stirred at room temperature for 2 h to consume the R-hydroxy-tosylate R-6 by tlc analysis. The mixture was diluted with ether (20 mL), washed with 1N HCl (2×10 mL) and saturated NaHCO$_3$ (10 mL), dried (MgSO$_4$), and concentrated to afford crude 1-tosyloxy-2-R-($\alpha$-methoxy-$\alpha$-trifluoromethylphenylacetoxy)-3-butene(R,R-8), which was analyzed by $^1$H nmr without further purification.

$^1$H nmr (300 MHz, CDCl$_3$): 7.800 (2H, d, J=8.25 Hz); 7.356 (2H, d, J=8.19 Hz); 5.751 (1H, ddd, J=5.38, 10.46, 16.55 Hz); 5.378 (1H, br d, J=17.05 Hz); 5.247 (1H, br d, J=10.48 Hz); 4.396 (1H, m); 4.066 (1H, dd, J=3.39, 10.20 Hz); 3.906 (1H, dd, J=7.41, 10.22 Hz); 2.451 (3H, s); 2.276 (1H, d, J=4.50 Hz). IR (KBr, cm$^{-1}$): 3520 (s, b); 1650 (w); 1600 (s); 1350 (s); 1170 (s). Anal. Calcd for C$_{11}$H$_{14}$O$_4$S: C, 54.53; H, 5.82; N, O. Found: C, 54.84; H, 5.86; N, <0.3.

R,R-8;

$^1$H nmr (300 MHz, CDCl$_3$): 7.746*, 7.672* (2H, 2xd, J=8.26 Hz); 7.5-7.2 (7H, m); 5.5-5.25 (2H, m); 4.2-4.0 (2H, m); 3.539*, 3.475* (3H, 2xs); 2.445 (3H, s). IR (neat film, cm$^{-1}$): 1750 (s); 1600 (m); 1370 (s); 1175 (s). FDMS (m/z): 458 (M+). *Integration of either of these pairs of peaks gave the diastereomeric excess of 9.

Examples I–IV demonstrate the inventive method where an acyclic vinyl epoxide is reacted with water, with the reaction conditions varied. Reaction Scheme 5 is a representation of the reactions of Examples I–IV.

Reaction Scheme 5

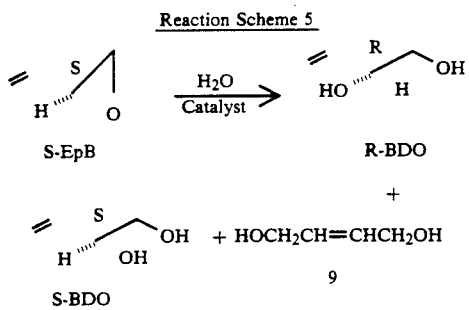

EXAMPLE I

To 5 mL of distilled water was added 17 μL of 3M aqueous H$_2$SO$_4$ (0.05 mmol; 0.01 molar equiv). To this solution was added dropwise 400 μL (5.0 mmol) of optically pure S-EpB (>98% ee)([α]D$^{20}$ +8.3° (c. 6.959, i-PrOH), literature for S-EpB, [α]D$^{25}$ +8.306 (c. 6.959, i-PrOH), Crawford et al., Can. J. Chem, 1976, 54, 3364. The resulting homogeneous solution was stirred at room temperature for 15 min. No residual EpB was observed by capillary vpc (vapor phase chromatography) analysis. The reaction mixture was then neutralized to pH 7–9 by the addition of several drops of saturated aqueous NaHCO$_3$ The water was then removed at reduced pressure, and the residue was triturated with dichloromethane (20 mL), dried (Na$_2$SO$_4$), and concentrated to afford 82% of a 90:10 mixture of R-(+)-BDO and the isomeric product 2-butene-1,4-diol(9), respectively. The detection of 9 (and any other impurities) was carried out by $^1$H nmr (nuclear magnetic resonance) analysis. The optical purity of the R-BDO thus produced was determined to be 92% ee by the analysis described above. Results of all Examples are summarized in TABLE I (following the Comparative Examples). The achiral properties of BDO are as described below.

BDO:
$^1$H nmr (300 MHz, CDCl$_3$): 5.842 (1H, ddd, J=5.52, 10.51, 16.89 Hz); 5.350 (1H, dd, J=1.67, 17.08 Hz); 5.222 (1H, dd, J=1.07, 10.38 Hz); 4.25 (1H, m); 3.670 (1H, dd, J=3.34, 11.26 Hz); 3.493 (1H, dd, J=7.42, 11.26 Hz); 2.572 (2H, br s). EIMS (m/z): 70 (M$^+$-H$_2$O); 57 (M$^+$-CH$_2$OH). IR (neat film, cm$^{-1}$): 3340 (s, b); 2920 (m); 2870 (m); 1640 (w).

9:
$^1$H nmr (300 MHz, CDCl$_3$); 5.765 (2H, t, J=4.18 Hz); 4.203 (4H, d, J=4.20 Hz); 2.781 (2H, br s).

EXAMPLE II

The procedure of Example I was followed in an identical manner except that the solution of water and H$_2$SO$_4$ was cooled to 5° C. in an ice-water bath prior to the addition of the S-EpB. The resulting homogeneous solution was stirred at 5° for 45 min., at which time substantially all EpB had been consumed according to vpc analysis (after 15 min residual EpB was observed). The acid was neutralized to pH 7–9 by the addition of several drops of saturated aqueous NaHCO$_3$, and the solvent was removed at reduced pressure. The residue was triturated with dichloromethane (20 mL), dried (Na$_2$SO$_4$), and concentrated to afford 330 mg (75%) of a 95:5 mixture of R-(+)-BDO and 9, respectively, by $^1$H nmr analysis. The optical purity of the R-BDO thus produced was determined to be 94% ee. Results are summarized in TABLE I. All achiral properties of BDO are as described previously.

[α]D$^{20}$ +44.1° (c. 2.86, i-PrOH) (rotation corrected for the presence of achiral 9).

EXAMPLE III

The procedure was similar to that described in Example 1 except that S-EpB was added to a 1M sulfuric acid solution (1.67 mL of 3.0M H$_2$SO$_4$ and 3.33 mL H$_2$O; pH 0) at room temperature. The mixture was stirred at room temperature for 1 h to afford 339 mg (77% total) of an 89:11 mixture of R-(+)BDO and 9, respectively (1H nmr analysis). In the manner described previously, the optical purity of the BDO was determined to be 82% ee.

[α]D$^{20}$ +37.6° (c. 2.804, i-PrOH)(rotation corrected for the presence of achiral 9).

EXAMPLE IV

The procedure was similar to that described in Example 1 except that S-EpB (5 mmol) was added to p-toluene sulfonic acid hydrate (p-TSA, 48 mg; 0.25 mmol; 0.05 equiv) in 5 mL of water at room temperature. EpB was substantially consumed after 1 h (vpc analysis) and workup afforded 365 mg (83% total) of R-(+)-BDO contaminated with 12% of 9 and a small amount of p-TSA. In the manner described previously, the optical purity of R-BDO was determined to be 84% ee. Results are summarized in TABLE I. [α]D$^{20}$ +39.7° (c. 2.662, i-PrOH) (rotation corrected for the presence of achiral 9).

Examples V–VII demonstrate the inventive method where an acylic vinyl epoxide is reacted with different alcohols. Reaction Scheme 6 is a representation of the reactions of Examples V–VII where R' is defined individually for each example.

Reaction Scheme 6

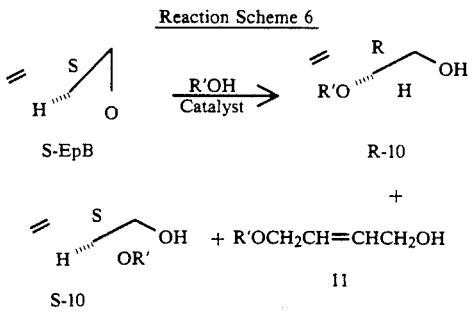

EXAMPLE V

The procedure was similar to that described in Example 1 except that CH$_3$OH was substituted for the water component (R' is —CH$_3$), thus forming R-2-methoxy-3-butene-1-ol (R-10a), in the following manner. Substantially optically pure S-EpB (350 mg; 5.0 mmol) was dissolved in methanol (5 mL) and cooled to 0° C. A catalytic amount of sulfuric acid (3M; 17 μL; 0.05 mmol; 0.01 equiv) was added and the reaction mixture was stirred at 0° C. for 1 h and then warmed to room temperature for 1 h. Solid sodium bicarbonate (10 mg) was added, and the solvent was removed at reduced pressure. The residue was triturated with dichloromethane, diluted with ether, dried (MgSO4), and concentrated to afford 379 mg (74%) of the mixture of 2-methoxy-3-butene-1-ol (R-10a) and the isomeric product 4-methoxy-2-butene-1-ol (11a). $^1$H nmr analysis indicated a ratio of 10a:11a of 95:5, while capillary vpc (vapor phase chromatography) using a chiral Cyclodex-B column indicated >98% ee for R-10a. Results are summarized in TABLE I.

R-10a:

$^1$H nmr (300 MHz' CDCl$_3$): 5.658 (1H, ddd, J=7.35, 9.94, 17.52 Hz); 5.313 (1H, d, J=19.08 Hz); 5.297 (1H, d, J=9.71 Hz); 3.698 (1H, m); 3.55 (2H, m); 3.332 (3H, s); 2.217 (1H, br s ). IR (neat film, cm$^{-1}$): 3400 (s, b); 1640 (w). EIMS (m/z): 101 (M+-H), 85 (M+-OH), 71 (M+-CH$_2$OH). [α]D$^{20}$-44.8° (c. 0.995, methanol)

EXAMPLE VI

Example I was followed with the exception that CH$_3$CH$_2$OH was substituted for the water component (R' is —CH$_2$CH$_3$), thus forming R-2-ethoxy-3-butene-1-ol (R-10b), in the following manner. Sulfuric acid (3M; 17 μL; 0.05 mmol; 0.01 equiv) was dissolved in 5 mL of ethanol and cooled to 0° C. Optically pure S-EpB (350 mg; 5.0 mmol) was added dropwise and the reaction mixture was allowed to warm to room temperature. After 1.5 h at room temperature EpB had been substantially consumed according to vpc analysis. Excess solid sodium bicarbonate was added, and the solvent was removed at reduced pressure. The residue was triturated with dichloromethane (10 mL) and ether (10 mL), dried (Na2SO4), and concentrated to afford 454 mg (78%) of a 92:8 mixture of R-10b:11b (4-ethoxy-2-butene-1-ol) according to $^1$H nmr analysis. Capillary vpc analysis using a chiral Cyclodex-B column indicated 95.6% ee for R-10b. Results are summarized in TABLE I.

R-10b:

$^1$H nmr (300 MHz, CDCl$_3$): 5.692 (1H, ddd, J=7.17, 10.34, 17.4 Hz); 5.308 (1H, d, J=16.86 Hz); 5.264 (1H, d, J=9.58 Hz); 3.82 (1H, m); 3.7–3.45 (3H, m); 3.394 (1H, dd, J=7.00, 9.34 Hz); 2.065 (1H, br s); 1.208 (3H, t, J=7.01 Hz). IR (neat film, cm$^{-1}$): 3420 (s, b); 1640 (w).

EXAMPLE VII

Example I was followed with the exception that (CH$_3$)$_2$CHOH was substituted for the water component [R' is —CH(CH$_3$)2], thus forming R-2-(2-Methylethoxy)-3-butene-1-ol (R-10c), in the following manner. Sulfuric acid (3M; 17 μL; 0.05 mmol; 0.01 equiv) was dissolved in 5 mL of isopropanol and cooled to 0° C. Substantially optically pure S-EpB (350 mg; 5.0 mmol) was added dropwise and the reaction mixture was allowed to warm to room temperature and stirred overnight (20 h) to completely consume EpB by vpc analysis. Excess solid sodium bicarbonate was added, and the solvent was removed at reduced pressure. The residue was triturated with dichloromethane (10 mL) and ether (10 mL), dried (Na2SO4), and concentrated to afford 455 mg (70%) of a 84:16 mixture of R-10c:11c [4-(2-methylethoxy)-2-butene-1-ol]by $^1$H nmr analysis. Capillary vpc analysis using a chiral Cyclodex-B column indicated 88.4% ee for R-10c. Results are summarized in TABLE I.

R-10c:

$^1$H nmr (300 MHz, CDCl$_3$): 5.705 (1H, ddd, J=6.95, 10.40, 17.32 Hz); 5.300 (1H, d, J=17.53 Hz); 5.231 (1H, d, J=10.49 Hz); 3.95 (1H, m); 3.700 (1H, m(7), J=6.11 Hz); 3.539 (1H, dd, J=3.65, 10.93 Hz); 3.474 (1H, dd, J=7.64, 11.22 Hz); 2.085 (1H, br s); 1.169 (3H, d, J=6.17 Hz); 1.148 (3H, d, J=5.98 Hz). IR (neat film, cm$^{-1}$): 3430 (s, b); 1640 (w).

Comparative Examples I–IX illustrate the reaction of acylic vinyl expoxides with water in non-acidic media.

COMPARATIVE EXAMPLE I

The procedure was similar to that described in Example I except that S-EpB (5 mmol) was stirred with 1N NaOH (5 mL) and afforded R-(+)-BDO contaminated with various other materials (352 mg crude). As analyzed by the techniques previously described, the R-BDO was found to possess 30% ee, as shown in TABLE I.

COMPARATIVE EXAMPLE II

The procedure was similar to that described in Example I except that S-EpB (5 mmol) was stirred with potassium carbonate (1.04 g; 7.5 mmol; 1.5 equiv) at room temperature for 10 days to consume EpB. Workup afforded R-(+)-BDO free of 9 (343 mg, 78%) as determined by $^1$H nmr analysis. As analyzed by the techniques previously described, the R-BDO was found to possess 46% ee, as shown in TABLE I.

[α]D$^{20}$ +23.5° (c. 3.130, i-PrOH).

COMPARATIVE EXAMPLE III

The procedure was similar to that described in Example I except that S-EpB (5mmol) was stirred for 14 days in 5 mL of aqueous pH 7 phosphate buffer (VWR scientific). Workup afforded R-(+)BDO (72%) contaminated with 1% 9 as determined by $^1$H nmr analysis. As analyzed by the techniques previously described, the R-BDO was found to possess 85% ee, as shown in TABLE I.

[α]D$^{20}$ +38.6° (c. 3.025, i-PrOH).

COMPARATIVE EXAMPLE IV

The procedure was similar to that described in Example I except that S-EpB (5 mmol) was stirred in water (5 mL) at room temperature for 2.5 days to afford 122 mg (28%) of R-(+)-BDO free of 9 as determined by $^1$H nmr analysis. As analyzed by the techniques previously described, the R-BDO was found to possess 87% ee, as shown in TABLE I.

[α]D$^{20}$ +41.1° (c. 1.080, i-PrOH).

COMPARATIVE EXAMPLE V

The procedure was similar to that described in Example I except that S-EpB (5 mmol) was stirred in water (5 mL) at room temperature for 10 days to afford R-(+)-BDO (65%) free 9 as determined by $^1$H nmr analysis. As analyzed by the techniques previously described, the R-BDO was found to possess 84% ee, as shown in TABLE I.

[αD$^{20}$ +39.5° (c. 2.990, i-PrOH).

COMPARATIVE EXAMPLE VI

The procedure was similar to that described in Example I except that S-EpB (5mmol) was stirred in water (5 mL) at 45° C. for 50 h. The reaction did not completely consume the EpB, and workup at this point afforded R-(+)-BDO (189 mg; 43%) free of 9 as determined by $^1$H nmr analysis. As analyzed by the techniques previously described, the R-BDO was found to possess 80% ee, as shown in TABLE I.

[α]D$^{20}$ +37.4° (c. 2.970, i-PrOH).

COMPARATIVE EXAMPLE VII

The procedure was similar to that described in Example 1 except that S-EpB (5 mmol) was stirred in water (5 mL) at 65° C. and allowed to react for 30 h to afford 246 mg (56%) of R-(+)-BDO free of 9 as determined by $^1$H nmr analysis. As analyzed by the techniques previously described, the R-BDO was found to possess 80% ee, as shown in TABLE I.

$[\alpha]D^{20}$ +37.8° (c. 3.020, i-PrOH).

COMPARATIVE EXAMPLE VIII

The procedure was similar to that described in Example 1 except that S-EpB (5 mmol) was added to water at 65° C., and the mixture was then heated to 100° C. for 3 hours to afford 128 mg (29%) of R-(+)-BDO contaminated with 1% of 9 as determined by $^1$H nmr analysis. As analyzed by the techniques previously described, the R-BDO was found to possess 72% ee, as shown in TABLE I.

$[\alpha]D^{20}$ +33.3° (c. 1.245, i-PrOH).

COMPARATIVE EXAMPLE IX

The procedure was similar to that described in Example 1 except that S-EpB (5 mmol) was added to water (5 mL) containing Amberlyst 15 ™ (17,5 mg; 5 wt. %) (obtained from Aldrich Chemical Co.). The reaction mixture was stirred at room temperature overnight at which time the EpB was consumed as indicated by vpc analysis. The catalyst was removed by filtration and isolation as above afforded R-(+)-BDO contaminated with 10% 9 by $^1$H nmr analysis (242 mg; 55% total). As analyzed by the techniques previously described, the R-BDO was found to possess 86% ee, as shown in TABLE I.

$[\alpha]D^{20}$ +40.6° (c. 2.77, i-PrOH) (rotation corrected for the presence of achiral 9).

TABLE I

| Example # | R'OH | Catalyst | R-BDO[1] | S-BDO[2] | BDO:9[3] | % ee | Total Yield |
|---|---|---|---|---|---|---|---|
| I | H$_2$O | H$_2$SO$_4$ (1 mole %) | 96[b] | 4[b] | 90:10 | 92% | 82% |
| II | H$_2$O | H$_2$SO$_4$ (1 mole % 5° C.) | 97[b] | 3[b] | 95:5 | 94% | 75% |
| III | H$_2$O | H$_2$SO$_4$ (100 mole %) | 91[b] | 9[b] | 89:11 | 82% | 77% |
| IV | H$_2$O | p-TSA | 92[c] | 8[c] | 88:12 | 84% | 83% |
| V | CH$_3$OH | H$_2$SO$_4$ | 99.2[d] | 0.8[d] | 95:5 | 98.4% | 79% |
| VI | CH$_3$CH$_2$OH | H$_2$SO$_4$ | 97.8[d] | 2.2[d] | 92:8 | 95.6% | 78% |
| VII | (CH$_3$)$_2$CHOH | H$_2$SO$_4$ | 94.2[d] | 5.8[d] | 84:16 | 88.4% | 70% |
| C.E.I[a] | H$_2$O | NaOH | 47.5[e] | 52.5[e] | >99:1 | 30% | 80% |
| C.E.II[a] | H$_2$O | K$_2$CO$_3$ | 73[b] | 27[b] | >99:1 | 46% | 78% |
| C.E.III[a] | H$_2$O | phosphate buffer | 92.5[e] | 7.5[e] | 99:1 | — | 72% |
| C.E.IV[a] | H$_2$O (25 days) | — | 93.5[b] | 6.5[b] | >99:1 | 87% | 28% |
| C.E.V[a] | H$_2$O (10 days) | — | 92[b] | 8[b] | >99:1 | 84% | 65% |
| C.E.VI[a] | H$_2$O (45° C., 50 hours) | — | 90[e] | 10[e] | — | 80% | 43% |
| C.E.VII[a] | H$_2$O (65° C., 30 hours) | — | 90[e] | 10[e] | — | 80% | 56% |
| C.E.VIII[a] | H$_2$O (100° C., 3 h) | — | 86[b] | 14[b] | 99:1 | 72% | 29% |
| C.E.IX[a] | H$_2$O | Amberlyst 15 ™ | 93[c] | 7[c] | 90:10 | 86% | 55% |

[1] or R-10 where applicable
[2] or S-10 where applicable
[3] or 10:11 where applicable
[a] Comparative Examples
[b] Enantiomeric ratio determined by comparison of optical rotation of the BDO produced with the maximum value of +47.0° calculated from the optical rotation ($[\alpha]_D^{20}$ +41.1°) and known optical purity (87% ee) from Example IV.
[c] Enantiomeric ratio determined by conversion of the BDO to 1-tosyloxy-3-buten-2-yl R-α-methoxy-α-trifluoromethylphenylacetate and integration of the diastereomeric signals by $^1$H nmr as previously described.
[d] Determined by capillary vpc on a chiral Cyclodex-B column (J&W Scientific).
[e] Enantiomeric ratio determined by taking into account the presence of 2-butene-1,4 diol.

The following preparations detail the determination of the absolute configuration of 2-methoxy-3-butene-1-ol by independent synthesis, proving that methanolysis occurred with inversion of configuration. Thus, the negative rotation of R-1-benzyloxy-2-methoxy-3-butene (shown below as R-12) prepared below compares with S-(+)-1-benzyloxy-2-methoxy-3-butene) obtained by independent synthesis from S-BDO. Inversion of configuration was implicated for R-10b (Example VI) and R-10c (Example VII) by comparison with R-10a (Example V).

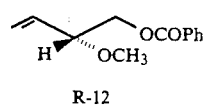

R-12

R-1-Benzyloxy-2-methoxy-3-butene R-12

Methyl ether R-10a (103 mg; 1.0 mmol) was dissolved in dichloromethane (1 mL). Triethylamine (0.21 mL; 1.5 mmol; 1.5 equiv) was added followed by benzoyl chloride (128 μL; 1.1 mmol; 1.1 equiv). The reaction mixture was stirred at room temperature for 2.5 days to completely consume R-10 by tlc analysis. The reaction mixture was diluted with ether (20 mL), washed with 1N HCl (2×10 mL) and saturated aqueous sodium bicarbonate (10 mL), dried (MgSO₄), and concentrated to afford 213 mg (>99%) of R-12.

R-12:
¹H nmr (300 MHz, CDCl₃): 8.058 (2H, d, J=7.32 Hz); 7.562 (1H, t, J=7.46 Hz); 7.439 (2H, t, J=7.41 Hz); 5.794 (1H, ddd, J=7.24, 10.32, 17.40 Hz); 5.398 (1H, d, J=18.43 Hz); 5.349 (1H, d, J=11.12 Hz); 4.385 (1H, dd, J=4.50, 11.48 Hz); 4.321 (1H, dd, J=6.51, 11.52 Hz); 3.984 (1H, q, J=6.50 Hz); 3.383 (3H, s). IR (neat film, cm⁻¹): 1720 (s); 1600 (m). EIMS (m/z): 176 (M⁺-CH₂O); 84 (M⁺-PhCOOH). [α]D²⁰-21.5° (c. 1.020, methanol).

Configuration Determination:
S-1-Benzoyloxy-2-hydroxy-3-butene (S-13)

S-BDO (125 mg; 1.42 mmol) was dissolved in dichloromethane and cooled to 0° C. Triethylamine (0.24 mL; 1.70 mmol; 1,2 equiv) was added followed by benzoyl chloride (148 μL; 1.28 mmol; 0.9 equiv). The reaction mixture was allowed to warm to room temperature overnight to completely consume benzoyl chloride by tlc analysis. The reaction mixture was diluted with ether (50 mL), washed with 1N HCl (2×15 mL) and saturated aqueous sodium bicarbonate (15 mL), dried (MgSO₄), and concentrated. The crude product was flash chromatographed and eluted with 30% ether in pentane to afford 171 mg (70%) of S-13.

S-13:
¹H nmr (300 MHz, CDCl₃): 8.057 (2H, d, J=7.41 Hz); 7.579 (1H, t, J=7.47 Hz); 7.450 (2H, t, J=7.72 Hz); 5.950 (1H, ddd, J=5.47, 10.50, 16.36 Hz); 5.453 (1H, d, J=17.29 Hz); 5.289 (1H, d, J=10.45 Hz); 4.53 (1H, m); 4.432 (1H, dd, J=3.53, 11.47 Hz); 4.298 (1H, dd, J=7.14, 11.43 Hz); 2.27 (1H, br s). IR (neat film, cm⁻¹): 1400 (s, b); 1715 (s); 1600 (w); 1580 (w). FDMS (m/z): 192 (M⁺).
[α]D²⁰-6.0° (c. 1.066, methanol).

S-1-Benzoyloxy-2-methoxy-3-butene (S-12)

Powdered potassium hydroxide (83 mg; 1.48 mmol; 2.5 equiv) was slurried in DMSO (2.5 mL) and stirred for five min. Benzoate S-13 (114 mg; 0.593 mmol) was added in 2 mL of DMSO followed by iodomethane (74 μL; 1.2 mmol; 2 equiv). The reaction mixture was stirred for 45 min at room temperature to completely consume S-13 (tlc analysis) and then poured into 1:1 ether:pentane (50 mL). The organic solution was washed with water (5×20 mL), dried (MgSO₄), and concentrated. The crude product was flash-chromatographed and eluted with 1:9 ether:pentane to afford 33 mg (27%) of S-12. All achiral physical properties are as reported above.
[α]D²⁰ +18.0 (c. 0.662, methanol).

The invention has been described in detail with particular reference to preferred embodiments thereof, but it will be understood that variations and modifications can be effected within the spirit and scope of the invention. All patents, patent applications (published or unpublished, domestic or foreign), scientific literature, books and other prior art cited herein are each incorporated herein by reference for the teaching therein pertinent to this invention.

That which is claimed is:

1. A method for the interconversion of enantiomers of an acylic 1,2-dihydroxy-3-alkene or converting either enantiomer of an acylic 1,2-dihydroxy-3-alkene to a corresponding antipodal 1-hydroxy-2-alkoxy-3-alkene compound comprising reacting in an acidic reaction media either enantiomer of an acylic vinyl epoxide with water, an alcohol, or a mixture thereof to form a product comprising an inverted acylic 1,2-dihydroxy-3-alkene or an inverted 1-hydroxy-2-alkoxy-3-alkene compound.

2. A method according to claim 1 wherein said acyclic vinyl epoxide is substantially optically pure and said inverted product is substantially optically pure.

3. A method according to claim 2 wherein
(a) said acyclic vinyl epoxide is of the Formula I:

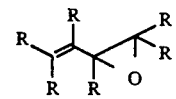

wherein R independently represents a straight or branched, substituted or unsubstituted, $C_1$-$C_{20}$ alkyl, $C_2$-$C_{20}$ alkenyl, or $C_2$-$C_{20}$ alkynyl group, or an unsubstituted or substituted $C_4$-$C_{10}$ aromatic or heteroaromatic group (with the hetero atom selected from nitrogen, sulfur, or oxygen), with said substituents designated above selected from one or more of the following: halogen, a cyano, a $C_1$-$C_5$ alkoxy, a $C_1$-$C_5$ alkylthio, a $C_1$-$C_5$ ether group, a $C_1$-$C_5$ ester group, a nitro group, a $C_1$-$C_5$ ketone group, or a $C_1$-$C_5$ thioether group, and (b) said alcohol is of the formula R'OH wherein R' represents an unsubstituted or substituted, straight or branched $C_1$-$C_{20}$ alkyl, $C_2$-$C_{20}$ alkenyl, or $C_2$-$C_{20}$ alkynyl group or an unsubstituted or substituted $C_4$-$C_{20}$ aromatic group (with said substituents designated above selected from one or more of the following: a halogen, a cyano, a $C_1$-$C_5$ alkoxy, a $C_1$-$C_5$ alkylthio, a $C_1$-$C_5$ ether group, a $C_1$-$C_5$ ester group, a nitro group, a $C_1$-$C_5$ ketone group, or a $C_1$-$C_5$ thioether group).

4. A method according to claim 3 wherein said epoxide is of the Formula II:

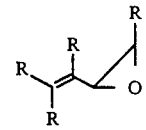

wherein R is as defined previously.

5. A method according to claim 4 wherein said epoxide is of the Formula III:

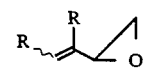

wherein R is as defined previously.

6. A method according to claim 5 wherein said pH level is from 0 to 7 and said reaction media is of a temperature as low as possible, while maintaining said reaction media as a liquid and said reaction having at least 80% of said acyclic vinyl epoxide substrate consumed within about 48 hours.

7. A method according to claim 6 wherein said reaction media is of a temperature between about 0° C, to about 25° C. and said reaction having at least 90% of said acyclic vinyl epoxide substrate consumed within 24 hours.

8. A method for the interconversion of enantiomers of an acyclic 1,2-dihydroxy-3-alkene compound comprising reacting in an acidic reaction media either enantiomer of an acylic vinyl epoxide with water to form a product comprising an inverted 1,2-dihydroxy-3-alkene compound.

9. A method according to claim 8 wherein said acyclic vinyl epoxide is substantially optically pure and said inverted product is substantially optically pure.

10. A method according to claim 9 wherein
(a) said acyclic vinyl epoxide is of the Formula I:

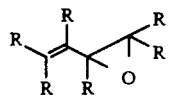   I wherein R independently represents a straight or branched, substituted or unsubstituted, $C_1$–$C_{20}$ alkyl, $C_2$–$C_{20}$ alkenyl, or $C_2$–$C_{20}$ alkynyl group, or an unsubstituted or substituted $C_4$–$C_{10}$ aromatic or heteroaromatic group (with the hetero atom selected from nitrogen, sulfur, or oxygen), with said substituents designated above selected from one or more of the following: halogen, a cyano, a $C_1$–$C_5$ alkoxy, a $C_1$–$C_5$ alkylthio, a $C_1$–$C_5$ ether group, a $C_1$–$C_5$ ester group, a nitro group, a $C_1$–$C_5$ ketone group, or a $C_1$–$C_5$ thioether group.

11. A method according to claim 10 wherein said epoxide is of the Formula II:

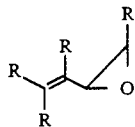   II wherein R is as defined previously.

12. A method according to claim 11 wherein said epoxide is of the Formula III:

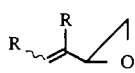   III wherein R is as defined previously.

13. A method according to claim 12 wherein said pH level is from 0 to 7 and said reaction media is of a temperature as low as possible, while maintaining said reaction media as a liquid and said reaction having at least 80% of said acyclic vinyl epoxide substrate consumed within about 48 hours.

14. A method according to claim 13 wherein said reaction media is of a temperature between about 0° C. to about 25° C. and said reaction having at least 90% of said acyclic vinyl epoxide substrate consumed within 24 hours.

15. A method for converting either enantiomer of an acylic 1,2-dihydroxy-3-alkenes comprising reacting in an acidic reaction media either enantiomer of an acylic vinyl epoxide with an alcohol to form an inverted acyclic 1-hydroxy-2-alkoxy-3-alkene compound.

16. A method for according to claim 15 wherein
(a) said acyclic vinyl epoxide is of the Formula I:

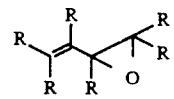   I wherein R independently represents a straight or branched, substituted or unsubstituted, $C_1$–$C_{20}$ alkyl, $C_2$–$C_{20}$ alkenyl, or $C_2$–$C_{20}$ alkynyl group, or an unsubstituted or substituted $C_4$–$C_{10}$ aromatic or heteroaromatic group (with the hetero atom selected from nitrogen, sulfur, or oxygen), with said substituents designated above selected from one or more of the following: halogen, a cyano, a $C_1$–$C_5$ alkoxy, a $C_1$–$C_5$ alkylthio, a $C_1$–$C_5$ ether group, a $C_1$–$C_5$ ester group, a nitro group, a $C_1$–$C_5$ ketone group, or a $C_1$–$C_5$ thioether group; and
(b) said alcohol of the formula R'OH wherein R' represents an unsubstituted or substituted, straight or branched $C_1$–$C_{20}$ alkyl, $C_2$–$C_{20}$ alkenyl, or $C_2$–$C_{20}$ alkynyl group or an unsubstituted or substituted $C_4$–$C_{20}$ aromatic group (with said substituents designated above selected from one or more of the following: a halogen, a cyano, a $C_1$–$C_5$ alkoxy, a $C_1$–$C_5$ alkylthio, a $C_1$–$C_5$ ether group, a $C_1$–$C_5$ ester group, a nitro group, a $C_1$–$C_5$ ketone group, or a $C_1$–$C_5$ thioether group).

17. A method according to claim 16 wherein said epoxide is of the Formula II:

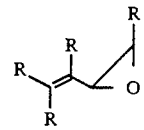   II wherein R is as defined previously; R' is selected from the group consisting of a $C_1$ to $C_6$ straight or branched alkyl group.

18. A method according to claim 17 wherein said epoxide is of the Formula III:

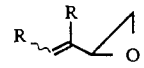   III wherein R is as defined previously.

19. A method according to claim 18 wherein said pH level is from 0 to 7, and said reaction media is of a temperature as low as possible, while maintaining said reaction media as a liquid and said reaction having at least 80% of said acyclic vinyl epoxide substrate consumed within about 48 hours.

20. A method according to claim 19 wherein said reaction media is of a temperature between about 0° C. to about 25° C. and said reaction having at least 90% of said acyclic vinyl epoxide substrate consumed within 24 hours.

* * * * *

UNITED STATES PATENT AND TRADEMARK OFFICE
CERTIFICATE OF CORRECTION

PATENT NO. : 5,250,743
DATED : October 5, 1993
INVENTOR(S) : Neil W. Boaz

It is certified that error appears in the above-identified patent and that said Letters Patent is hereby corrected as shown below:

Title page, item [54] "INTERCOVERSION" should read --INTERCONVERSION--
    Col. 10, line 53 should read  --R-6:--
    Col. 11, lines 5-19 correct Reaction Scheme 5 should read:

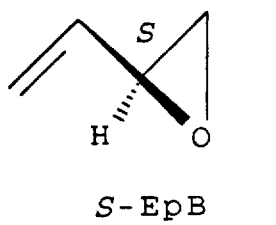

S-EpB

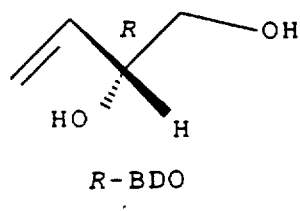

R-BDO

+

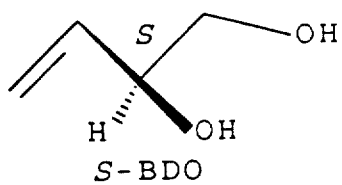  +  $HOCH_2CH=CHCH_2OH$

S-BDO                 9

UNITED STATES PATENT AND TRADEMARK OFFICE
CERTIFICATE OF CORRECTION

PATENT NO. : 5,250,743  Page 2 of 3
DATED : October 5, 1993
INVENTOR(S) : Neil W. Boaz It is certified that error appears in the above-identified patent and that said Letters Patent is hereby corrected as shown below:

Col. 12, Lines 41-55 correct Reaction Scheme 6 should read:

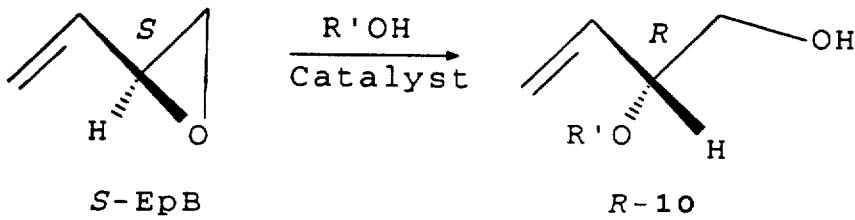

+

UNITED STATES PATENT AND TRADEMARK OFFICE
CERTIFICATE OF CORRECTION

PATENT NO. : 5,250,743
DATED : October 5, 1993
INVENTOR(S) : Neil W. Boaz

It is certified that error appears in the above-indentified patent and that said Letters Patent is hereby corrected as shown below:

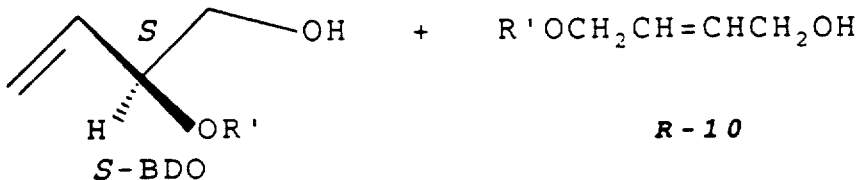

Signed and Sealed this

Twenty-second Day of March, 1994

Attest:

BRUCE LEHMAN

Attesting Officer     Commissioner of Patents and Trademarks